United States Patent [19]

Wagner et al.

[11] Patent Number: 5,032,407
[45] Date of Patent: Jul. 16, 1991

[54] GENE TRANSFER USING TRANSFORMED, NEODETERMINED, EMBRYONIC CELLS

[75] Inventors: Thomas E. Wagner; Michael A. Reed; Barbara J. Corn, all of Athens, Ohio

[73] Assignee: Ohio University Edison Animal Biotechnology Center, Athens, Ohio

[21] Appl. No.: 4,077

[22] Filed: Jan. 16, 1987

[51] Int. Cl.$^5$ .................. A61K 35/00; C12N 15/00; C12N 5/00
[52] U.S. Cl. ...................................... 424/520; 424/93; 424/582; 435/172.3; 435/240.2; 800/2; 935/62
[58] Field of Search ............... 435/172.3, 240.2; 800/1, 2, DIG. 2; 424/520, 582, 93; 935/62

[56] References Cited

U.S. PATENT DOCUMENTS 4,497,796 2/1985 Salser et al. ................. 424/95

OTHER PUBLICATIONS

Anderson, French W., "Prospects for Human Gene Therapy", Science 226:401 (1984).
"Differential Susceptibility of Mouse Trophoblast and Embryonic Tissue to Immune Cell Lysis", Jenkinson and Billington, Transplantation, 18:286–88 (1974).
"Transplantation of Fetal Hematopoietic Stem Cells in Utero: The Creation of Hamatopoietic Chimeras", Flake, et al., Science, 233:776–78 (1986).
"Introduction of a Selectable Gene into Primitive Stem Cells Capable of Long-Term Reconstitution of the Hemopoietic System of W/W$^v$ Mice", Dick, et al., Cell, 42:71–79 (1985).
"Retrovirus Transfer of a Bacterial Gene into Mouse Haematopoietic Progenitor Cells", Joyner, et al., Nature, 305:556–559 (1983).
Studies on the Immunobiology of Mouse Fetal Membranes: "The Effect of Cell-Mediated Immunity of Yolk Sac Cells in Vitro", J. Reprod. Fert., 41:403–412 (1974).
Billington and Jenkinson, "Antigen Expression During Early Mouse Development", Balls and Wild, The Early Development of Mammals, 219–232, (1975).
Ritter, "Early Differentiation of the Lymphoid System", Balls and Wild, The Early Development of Mammals, 359–372 (1975).
"Factors Regulating Yolk Sac Hematopoiesis in Diffusion Chambers: Various Types of Sera, Cyclophosphamide, Irradiation and Long-Term Culture", Weinberg and Stohlman, Jr., Exp. Hematol., 5:374–384 (1977).
"An in vitro Morphological Study of the Mouse Visceral Yolk Sac and Possible Yolk Sac Immunocyte Precursors", Cell Tissue Res., 113–119 (1977).
"Hemopoiesis and Blood Vessels in Human Yolk Sac", Hesseldahl and Larsen, Acta. Anat. 78:271–291 (1971).
"Initial Growth of Transplanted E11 Fetal Cortex and Spinal Cord in Adult Rat Spinal Cord", Bernstein, et al., Brain Research 343:336–345 (1985).
"Establishment in Culture of Pluripotential Cells from Mouse Embryos", Evans and Kaufman, et al., Nature, 292:154–156 (1981).
"Some Aspects of Tissue Interaction in Vitro", Auerbachm Epithelical-Mesenchymal Interactions, Chap. 13, pp. 200–7 (1968).
"Evidence for the Time of Appearance of H-2 Antigens in Mouse Development," Patthey and Edidin, Transplantation, 15:211–214 (1973).
"Demonstration of Permanent Factor-Dependent Multipotential (Erythroid/Neutrophil/Basophil) Hematopoietic Progenitor Cell Lines", Greenberger, et al., P.N.A.S. (U.S.A.), 80:2931–35 (1983).
"Introduction of New Genetic Material into Pluripotent Haematopoietic Stem Cells of the Mouse", Williams, et al., Nature, 310:476–80 (1984).
"Gene Expression in Mice After High Efficiency Retroviral-Mediated Gene Transfer", Eglitis, et al., Science 230;1395–98 (1985).
"Amphotropic Retrovirus Vector Transfer of the v-ras Oncogene to Human Hematopoietic and Stromal Cells in Continuous Bone Marrow Cultures", Rothstein, et al., Blood, 65:744–752 (1985).
"Fetal Liver, A Source for Hemopoietic Reconstitution without GHVD?", Heit, et al., Biology of Bone Marrow Transplantation, 507–517 (Academic Press; 1980).
"Fetal Bone Grafts do not Elicit Allograft Rejection Because of Protecting Anti-Ia Alloantibodies", Segal, et al., Transplantation, 28:88–95 (1979).
"Transgenesis by Means of Blastocyst-Derived Embryonic Stem Cell Lines", Gossler et al., PNAS (U.S.A.) 83:9065–69 (Dec. 1986).

"Totipotent Hematopoietic Stem Cells: Normal Self-Renewal and Differentiation after Transplantation between Mouse Fetuses", Fleischman, et al., Cell, 30:351-59 (1982).

"Murine Yolk Sac Hematopoiesis Studied with the Diffusion Chamber Technique" Symann, et al., Exp. Hematol., 6:749-59 (1978).

Lovell-Badge et al., Cold Spring Harbor Symp. Quant. Biol., vol. L, pp. 707-712 (1985), Cold Spring Harbor Lab., New York.

Gossler et al., Proc. Natl. Acad. Sci. 83:9065-9 (1986).

Kuehn et al., Nature 326:295 (1987).

*Primary Examiner*—Elizabeth C. Weimar
*Assistant Examiner*—Jasemine C. Chambers
*Attorney, Agent, or Firm*—Iver P. Cooper

[57] ABSTRACT

This invention is directed to a method for the preparation of carrier cells capable of delivering exogenous genetic material to a particular tissue of the body by means of embryonic cells competent to develop into that tissue, and essentially only that tissue, said cells bearing the exogenous genetic material. The preferred carrier cells are mesodermal cells of the yolk sac or embryonic forebrain or midbrain cells, and the desired genetic material is preferably introduced into the cells by in vitro transformation with an amphotrophic retroviral vector.

15 Claims, 2 Drawing Sheets

GENE TRANSFER USING TRANSFORMED, NEODETERMINED, EMBRYONIC CELLS

BACKGROUND OF THE INVENTION

The invention relates to the use of early embryonic cells to deliver genetic material into a fully formed animal.

It is often desirable to confer upon an animal a particular genetic trait.

It is possible to remove bone marrow cells from the animal, transform them with a vector carrying the desired gene, and reimplant the transformed cells. Generally speaking, the transformed cells are given a competitive advantage. For example, the animal may be irradiated to partially or completely destroy the normal marrow, thus providing the transformed marrow cells with a vacant ecological niche. See, e.g., Joyner, et al., Nature (London), 305: 556 (1983). Clearly, this damage to the host is undesirable in a practical genetic delivery system.

Salser, U.S. Pat. Nos. 4,396,601 and 4,497,796 removed bone marrow cells from mice, cotransformed them with DNA including HSV DNA and the marker DHFR gene, and selected for cells resistant to methotrexate. These drug-resistant cells were injected into irradiated mice treated with methotrexate. Preferably, the bone marrow cell population used was one rich in hematopoietic stem cells. Salser does not teach use of cells removed from a mammalian embryo, and Salser severely stressed the recipient mice to give the modified cells a selective advantage.

Wagner et al, WO 82/04443 placed exogenous material into the pronucleus of a zygote. They teach that the zygote should be transformed as soon as possible after fertilization. We transform embryonic cells at a considerably later stage of development.

Mintz and Illmensee, PNAS 72:3585 (1975) injected teratocarcinoma (embryonal carcinoma, EC) cells into mouse blastocysts, obtaining mosaic mice. The teratocarcinoma cells proved to be developmentally totipotent, developing into a variety of normal tissues. This method cannot be used to deliver genes into specific tissues because the developmental course of these cells is uncertain. EC-like totipotent cells (EK cells) have also been obtained from culturing ICM cells of normal mouse embryos removed on day 2.5. Evans and Kaufman, Nature, 292:154 (1981).

We have found a convenient method for delivering genes into specific tissues of an animal which does not require extraction of any cells from the animal. Rather, we transform post-gastrular embryonic cells, which, besides being easier to culture, may be selected to be both (1) predestined to develop into the target tissue, and (2) essentially non-immunogenic.

One method known for the transformation of explanted cells involves use of a retroviral vector. See Vande Woude, U.S. Pat. No. 4,405,712.

When a retrovirus infects a cell, its RNA genome acts as a template for the reverse transcription of the viral genetic information into a double strand of DNA. This DNA molecule, now called a provirus, integrates into the genome of the host. Retroviral RNA is synthesized from the proviral sequence by the host's own RNA polymerase, and some of this RNA is translated into viral proteins. Under the instruction of the packaging sequence (called psi in the Moloney murine leukemia virus studies), the RNA-protein core of the virus is packaged into a glycoprotein envelope, and the resulting viral particle buds off from the cell into the medium (where it may find and infect other cells).

Mann, et al., Cell, 33:153 (1983) developed a cell line, known as psi-2, which is a line of NIH 3T3 cells with a permanently integrated helper virus. The helper virus, psi-minus, corresponds to the MoMLV with the psi sequence deleted by BalI-PstI cleavage. The psi-2 cells produce viral particles only when transformed by a retroviral vector bearing the psi sequence.

Cone and Mulligan, PNAS 81:6349 (1984), of the same research group, later developed an improved packaging cell line, psi-AM. This cell line was developed by transforming NIH 3T3 cells with a psi-minus chimera of an amphotrophic retrovirus (4070A). This amphotrophic murine retrovirus could infect non-murine hosts, including human and monkey cells.

Both psi-2 and psi-AM cells are readily available in the scientific community.

Joyner et al., supra, used an MoMLV retroviral vector to transfer a neomycin resistance gene into mouse hematopoietic progenitor cells. Williams, et al., Nature (London) 310: 476 (1984) used MSV DHFR-NEO transformed psi-2 cells to transfer neomycin resistance to co-cultivated bone marrow cells. See also Greenberger, et al., PNAS, 80:2931 (1983); Dick, et al., Cell, 42:71 (August 1985); Rubinstein, et al., 81:7137 (1984); Rothstein, et al., Blood, 65:744 (1985).

The above references teach retroviral transformation of "primitive but committed" non-embryonic cells. "Primitive" is a relative term, and these hematopoietic bone marrow stem cells are much further advanced in development than are the embryonic cells of the immediate post-gastrular stage ("neodetermined"), and therefore are likely to be less pluripotent and less histocompatible.

Verma, et al., in Tumor Viruses and Cell Differentiation, 251 (Scolnick and Levine, eds., 1983) and Miller, et al., PNAS (USA) 80: 4709 (1983) and Science, 225: 630 (1984) also describe use of retroviral vectors in gene therapy.

Genes may also be inserted by other techniques, such as calcium phosphate-mediated DNA uptake. Wigler, et al., Cell, 11: 223 (1977). To assure survival and proliferation of the transformed cells, powerful selection systems, such as DHFR/methotrexate, are used to inhibit untransformed cells. Carr, et al., Blood, 62: 180 (1983); Cline, et al., Nature, 284: 422 (1980). Without such selection, the efficiency of this procedure is presently too low to affect the recipient's condition significantly.

While Hammer, et al., Nature (London) 311: 65 (1984) has used microinjection of an RGH gene to correct dwarfism in the mouse, the technique is too labor intensive to be commercially practicable, even if other difficulties were overcome.

Lipid vesicles containing exogenous DNA have been injected into the tail vein of mice, so transformation occurs in vivo. Szoka, U.S. Pat. No. 4,394,448.

Kiester, Jr., Science 86, at 33 (March 1986) reports on research in which rat fetal brain tissue was grafted intraocularly into adult rats.

Jacob, EP Appl. 178,220 used a retroviral vector to confer G418 resistance on three embryonal carcinoma cell lines. He teaches implanting genetically engineered embryos into the uterus of a female mammal where it may naturally develop into a transgenic infant. This is to be distinguished from the present invention, in which engineered embryonic cells are injected into the bloodstream, or the corresponding tissue of the recipient. Jacob also teaches removing bone-marrow cells from a postnatal animal, transforming the cells, and returning them to the same animal.

Heit et al., in The Biology of Bone Marrow Transplantation, 507-517 (1980) suggested that fetal liver cells could be used for hematopoietic reconstitution without a graft versus host reaction. Mouse fetal liver cells have been microinjected into the placental circulation and thereby introduced into a recipient fetus. While this technique permits donor hematopoietic cells to become competitively established without ablation or irradiation of the recipient, it is dependent on the immunological immaturity of both donor cells and recipient. Fleischman, et al., Cell, 30:351-359 (1982); Flake, et al., Science, 233:776-778 (1986). Segal, et al., Transplantation, 28:88-95 (1979) suggests a mechanism whereby fetal bone grafts may escape host rejection in immunocompetent hosts.

Japanese application 61-81743 is said to relate to "a mature, non-human animal containing germ and somatic cells transformed by an activated tumor sequence, which was introduced into the animal or its ancestor during the fetal stage."

Yolk sac cells which produce an embryonic variant hemoglobin have been injected into irradiated adult mice of another strain and the surviving mice were found to be producing, in part, the donor adult type of hemoglobin. Auerbach, in EPITHELIAL-MESENCHYMAL INTERACTIONS, ch. 13 (1968).

SUMMARY OF THE INVENTION

This invention relates to the preparation of carrier cells capable of delivering genetic material to a particular tissue of the body by means of embryonic cells competent to develop into that tissue, and essentially only that tissue, said cells bearing the desired genetic material. The preferred carrier cells are mesodermal cells of the yolk sac or embryonal forebrain or midbrain cells, and the desired genetic material is preferably introduced into the cells by transformation with an amphotrophic retroviral vector. The yolk sac carrier cells are introduced intravenously. Preferably, the carrier cells may be introduced into an immunocompetent host without provoking an immune response.

Mammalian development may be divided into three distinct stages: the zygote, from fertilization to cleavage; the embryo, from cleavage to the formation of all somites; and the fetus, from the formation of the last somite until birth. This invention takes advantage of the unique properties of embryonic cells after their course of development is determined, but before they have lost immunoincompetency or the ability to proliferate rapidly.

An embryo begins with fertilization of an egg by a sperm. The fertilized egg is called a zygote. The unicellular zygote develops by successive mitotic divisions into a multicellular complex, the morula. The cells of the morula move outward to form a blastula. The daughter cells are called blastomeres, and are typically arrayed as a spherical layer, the blastoderm, surrounding a cavity, the blastocoele.

Gastrulation is the process by which the blastoderm differentiates into an ectoderm, a mesoderm, and an endoderm. The ectoderm will develop into the skin and nervous system; the mesoderm, into the muscular, skeletal, circulatory and excretory systems; and the endoderm, into the digestive system. For a number of organisms, "fate maps" have been constructed which show the normal developmental fate of each part of the blastula.

In the early gastrula stage, the prospective potency of the neural area of the ectoderm is such that if cells are transplanted to another area, they can develop into not only epidermis, but also mesodermal or endodermal tissues. At the end of gastrulation, a transplanted piece of presumptive neural tissue will differentiate as brain or spinal cord in whatever part of the embryo it is placed. Clearly, the surrounding tissues affected the development of the transplant. These inducing tissues act by releasing chemical inducers. By cultivating inductor tissues in suitable media, it is possible to produce "conditioned media" which contain effective amounts of the inducing substances.

The narrowing of the potency of the embryonic tissue is called determination. The range of developmental possibilities still open to a piece of tissue is its competency.

The first stage of development of the mammalian zygote is repeated cleavage into a solid mass of cells, the morula. The morula develops into a second structure, the blastocyst, having a distinct outer layer (the trophoblast) and an inner cell mass. The trophoblast enlarges and detaches from one side of the inner cell mass to create a yolk sac cavity, and the surface of the inner cell mass differentiates to form a hypoblast.

The trophoblast acts to attach the developing embryo to the walls of the uterus, a process known as implantation. The trophoblast cells become the placenta of the developing organism. The inner cell mass is destined to differentiate into ectodermal, mesodermal and endodermal tissues. Nonetheless, all of the ICM cells of the blastocyst are essentially totipotent, that is, they can develop into any tissue of the body. Evans and Kaufman, Nature, 292:154 (1981). It is only after gastrulation that their destiny is determined to some degree.

For one view of cell lineages in the mouse embryo, see FIG. 3 in Gardner and Papaiioannou, in THE EARLY DEVELOPMENT OF MAMMALS 107 (Balls and Wild, eds, Cambridge U:1975).

It is known that when completely undifferentiated cells of the blastula or morula are transplanted into a developed animal, they produce tumors. Id.

These totipotent, tumorigenic cells are of no value as genetic delivery systems. However, we have discovered that it is advantageous to transplant cells which have reached that stage of specialization at which they have become committed to a particular sequence of development, or lineage. Such cells may be used to deliver genetic material, or its expression products, into a particular tissue of the body, including blood cells.

The cells are transformed with genetic material of interest, transplanted into a host, and allowed to develop into the target tissue.

While it is necessary to use cells which have matured to the point of losing totipotency, overly mature cells will be rejected by the host. Consequently, it is desirable to use cells which have just lost totipotency. Such cells also retain the ability to colonize, thus facilitating their delivery to the target tissue.

Certain cells of the yolk sac offer particular advantages as tissue-specific genetic delivery means.

Unlike the cells of the embryo, the cells of the yolk sac develop into only a small number of different tissues. Among those tissues is the erythropoietic system, which includes the red and white blood cells, and the tissue of the veins, arteries and capillaries. Thus, by day 8 in the development of the mouse, mesodermal cells in the yolk sac have formed blood islets. The cells of the blood islets differentiate, the peripheral cells becoming the endothelium of the future blood vessels, and the central cells becoming first mesenchymal cells and then the red and white blood cells. The blood islands establish communications to form a circulatory network, which is extended into the embryo proper.

For the mouse, a standard reference work is Rugh, *The Mouse: Its Reproduction and Development*. According to this reference, gastrulation occurs at day 5.5. The mesoderm appears at day 6.5 as mesenchymal cells, and essentially separates the other two primary germ layers by day 7. The yolk sac is also formed by this time. Organogenesis begins at day 7.5 and the neural groove is formed by day 8. The circulatory system derives from blood islands, aggregations of mesenchymal cells in the mesoderm of the splanchnopleure. Blood cells are formed as early as day 7. By day 8, early forming blood islands and lacunae leading to vessels may be seen in the yolk sac. By day 8.5, blood islands are plentiful, and blood vessels are beginning to appear. By day 9, capillaries are also plentiful.

In the ectoderm, the prosencephalon (forebrain) and mesencephalon (midbrain) are both apparent by day 8. The neural crest develops on day 9.

Preferably, the yolk sacs are extracted prior to formation of visible (12X) blood islands.

Billington and Jenkinson, working with cells of the yolk sac of 10-14 day mouse embryos, found that these cells ex pressed both H-2 and non-H2 (major and minor histocompatibility) antigens. The work of Meyner (1973) and Patthey & Edidin (1973) cited by Billington and Jenkinson, reported that H2 antigens first appear on day 7 embryos, but the latter suggested that these antigens did not make an appearance in utero until day 9 or later. See THE EARLY DEVELOPMENT OF MAMMALS 219 (Balls and Wild, eds., Cambridge U.:1975).

We believe that the persistence of G-418-resistant yolk sac cells for three weeks after injection indirectly shows their ability to escape immune rejection. By contrast, research with bone marrow cells has depended on the use of immunocompromised hosts.

In another embodiment of this invention, embryonic yolk sac cells which do not necessarily contain exogenous DNA are introduced into an immunodeficient or hematopoieticdeficient host for purposes of hematopoietic reconstitution.

DETAILED DESCRIPTION OF THE INVENTION

EXAMPLE 1

Figure 1:
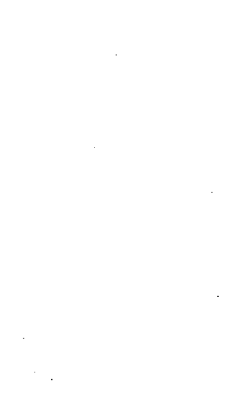
FIG. 1 is an autoradiograph showing the transfer of neomycin resistance to the bone marrow cell population using transformed, neodetermined cells.
Figure 1:
Figure 1:
Figure 1:
Figure 1:
Figure 1:
Figure 1:
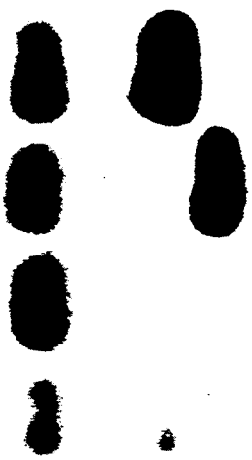
Figure 1:
Figure 1:
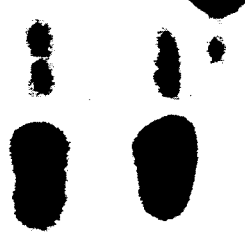
Figure 1:
Figure 2:
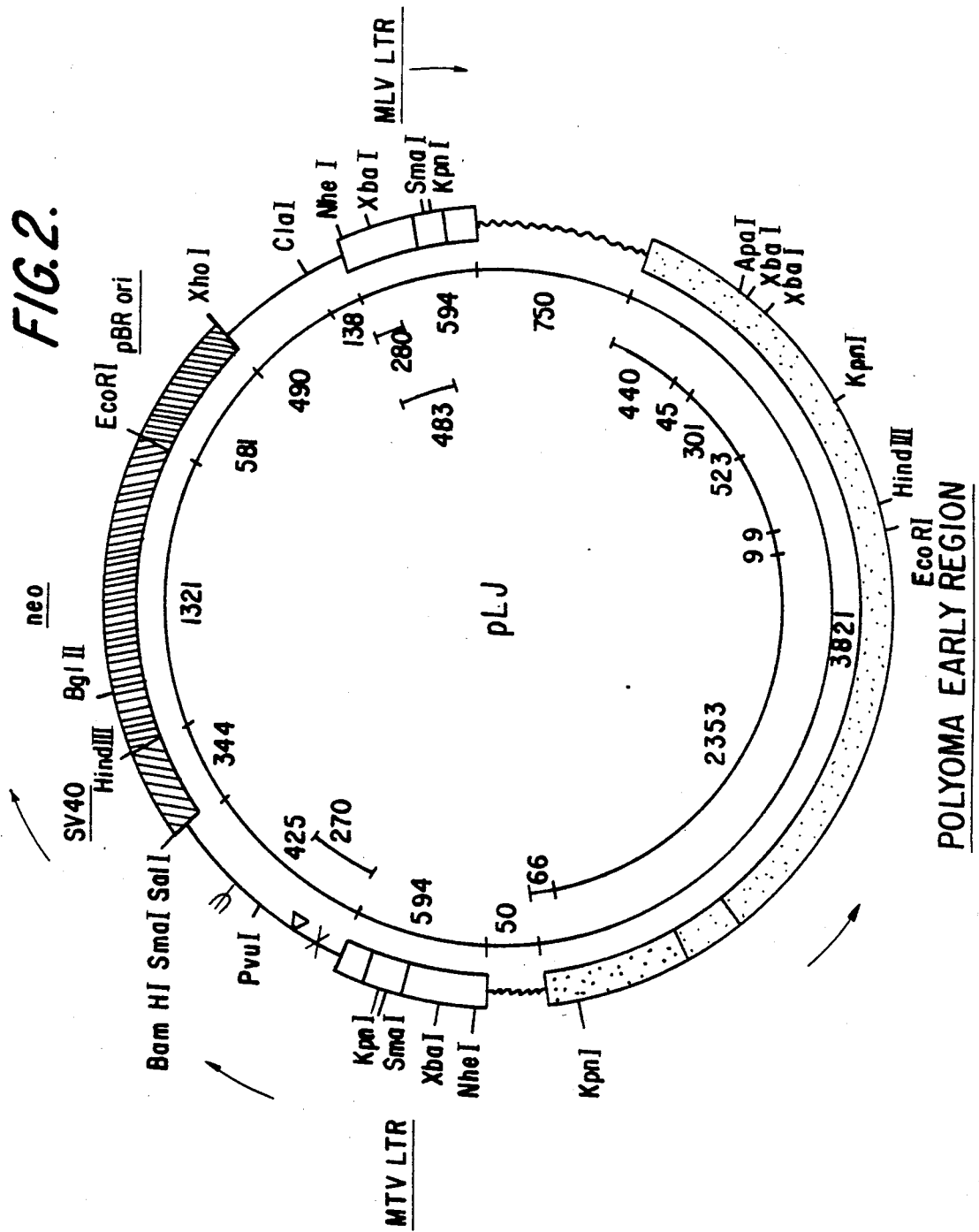
FIG. 2 is a map of the pLJ vector.

Cells of the yolk sac were surgically removed from a mouse embryo at day 7 or 8, physically disaggregated by drawing through a 21 gauge needle, and plated on culture media (Hams F12, 10% FCS, 10 ug/ml gentamicin). They aggregated to form spheres of yolk sac cells which attached themselves to the culture vessels. Physical disaggregation is preferred over enzymatic disaggregation using trypsin and collagenase.

Five different types of cells were identified in isolated yolk sacs: (1) a small, rounded cell; (2) a squamous epithelial cell; (3) a star-shaped cell appearing intermediate between (3a) fibroblast and (3b) epithelial cells; (4) a short, compact, dome-shaped fibroblast cell; and (5) a large, flat, basophilic epithelial cell believed to be the precursor of blood and lymphatic vessel cells. The last four types are believed to be mesodermal cells.

Mesodermal cells may be separated from endodermal cells by treatment with glycine according to Dziadek, Exper. Cell Res. 133:383 (1981).

EXAMPLE 2

The four mesodermal cell types were cloned by single cell dilution into conditioned media. The medium is preferably one used to support a mixed culture of yolk sac cells for 24 hours (see Example 1).

EXAMPLE 3

It is particularly advantageous to immortalize these primary cell lines. Immortalized cell lines may be produced from any of the five yolk sac cell types.

We have prepared immortalized mixed cultures, as well as an immortalized pure culture of yolk sac cell type (3). The primary cell line is grown to confluency in the original medium, thus selecting for cells which can grow under hypoxic conditions. Curatolo, et al., In Vitro, 20:597 (1984). Trypsin is used to dislodge the cells, and they are diluted 1:2 into fresh media. After 5-10 such passages, a crisis is reached at which most of the cells are inactive while a few, often polyploidal, are dividing rapidly. The latter are the immortalized cells, which may then be cloned and cultured.

These immortalized cell lines have the advantage that they may be maintained indefinitely in vitro.

EXAMPLE 4

In another embodiment of this invention, cells are surgically removed from the embryonic fore- and midbrain of a day 8 mouse embryo, disaggregated and cultured according to Example 1, and cloned according to Example 2. These cells have been immortalized by the method of Example 3.

EXAMPLE 5

The cells may now be transformed with the desired genetic material. While direct transformation is acceptable, it is preferable to use a vector, particularly a retroviral vector. The efficiency of retroviral transfer is higher.

Psi-2 cells are transformed with a modified pLJ retroviral vector (N2). In the pLJ vector, the viral genes (gag, pol, env) are deleted, but the packaging sequence and the LTR sequences (which are necessary for integration) remain. The modified pLJ vector used bears a transcriptional unit comprising an SV40 promoter, a neomycin resistance gene, and an SV40 terminator. See Eglitis, Science, 230:1395 (December 1985); Joyner, et al., nature, 305:556 (1983).

The psi-2 cells are placed in a medium containing modified pLJ retroviral particles. After several days cultivation, transformed cells are selected by killing untransformed cells with the mammalian cell toxin G418 [Gibco]. The expression product of the neomycin resistance gene phosphorylates and thereby inactivates G418, thus protecting the transformed cells. The cells are grown in the G418 media for about three weeks. A concentration of 500 ug/ml G418 is preferred.

In one embodiment of the invention, the yolk sac cells are cultivated in the supernatant from the transformed psi-2 cell culture. This supernatant contains the recombinant retroviral particles. The disadvantage of this approach is that the particles do not remain viable indefinitely.

Preferably, the yolk sac cells (pre-treated with polybrene) are co-cultivated with the transformed psi-2 cells, so they are continually exposed to the recombinant retroviral particles. If this is done, then there must be a way of distinguishing the transformed yolk sac cells from the transformed psi-2 cells, since both will carry neomycin resistance.

Mitomycin C destroys the ability of psi-2 cells to replicate, without hindering their production of retroviral particles. Psi-2 cells were treated with mitomycin C (concentration 2 ug/$10^6$ cells) at 50% confluency. While they cannot divide, they will still produce virus for several weeks. The yolk sac cells are added to the treated psi-2 cell culture. The viral particles produced by the psi-2 cells transfect the yolk sac cells. Eventually, after several subdivisions of the culture, the psi-2 cells die off, leaving only the yolk sac cells. Transformed yolk sac cells are then distinguished on the basis of resistance to G418.

Alternatively, psi-AM cells may be transfected with an amphotrophic retroviral vector and used to supply viral particles to the neodetermined carrier cells. Psi-AM cells are preferable to psi-2 cells in that they can carry a virus which is not species-specific.

EXAMPLE 6

Five day old newborn mice were intracranially injected with immortalized embryonic fore- and midbrain cells prepared according to Example 4. These cells had been transformed, as taught in Example 5, by a $Neo^R$-carrying retroviral vector in the presence of psi-2 helper cells. The mice were sacrificed after development to adulthood (five weeks old) and their brain cells were cultured.

EXAMPLE 7

We have demonstrated that by the method of this invention, heterologous genetic material (a neomycin resistance gene) was transferred to a specific tissue and measurably expressed by the recipient animal without ablation of the target tissue.

The tail vein of a 4 week mouse (ICR strain) was injected with 250–500,000 transformed (YS) cells. The animal was sacrificed and its spleen and bone marrow cells are examined for the presence of neomycin resistance genes.

The spleen cells (about $10^6$/well) were placed in suspension culture (RPMI 1640, 10% FCS, 25 mM HEPES buffer, 10 ug/ml gentamicin) with a T cell mitogen (phytohemagglutin, 25 ug/ml, Burroughs-Wellcome) in the presence of three different concentrations (500 ug/ml; 250 ug/ml; 125 ug/ml) of G418 for three days. The cells were assayed for the ability to replicate by measuring their uptake of tritiated thymidine. Tritiated thymidine (6.7 Ci/mmole) was added on the second day and the cells were harvested on the third day. Response of mice injected with YS cells (transformed with $neo^R$ bearing retrovirus) was compared with that of mice injected with psi-2 cells, and of mice which did not receive any cellular injection. Spleen cells from transformed YS cell injected animals cultured in 125 ug/ml G418 exhibited an activity which was 50.9% of that shown by spleen cells of control animals not exposed to G418. G418-treated spleen cells from psi-2 cell injected animals and control animals had activities of 40.3% and 39.7%, respectively. Thus, the injection of $neo^R$-transformed YS cells into the tail vein resulted in the expression of increased G418 resistance in the spleen.

In the table below, the counts are given, which are reflective of the cells' ability to replicate.

| | Control Mouse | | | | mean | |
|---|---|---|---|---|---|---|
| pHA, m | 51.2 | 6070.4 | 40.0 | 129.7 | | |
| cells, m | 629.0 | 213.4 | 1252.0 | 1323.3 | | |
| Cells, PHA | 2524.3 | 3193.7 | 2284.8 | 2158.9 | 2540 | |
| 500 | 536.6 | 313.1 | 372.1 | 457.0 | 419.7 | 16.5% |
| 250 | 757.3 | 619.9 | 1957.8 | 738.2 | 1018.1 | 40% |
| 125 | 1406.6 | 863.8 | 1119.0 | 645.7 | 1008.7 | 39.7% |
| | Psi-2 inj. mouse | | | | mean | |
| pHA, m | 76.2 | 82.7 | 104.3 | 73.0 | | |
| cells, m | 866.6 | 1154.5 | 693.3 | 863.4 | | |
| Cells, PHA | 10656.1 | 8156.3 | 8743.3 | 7092.4 | 8666.7 | |
| 500 | 1113.9 | 691.1 | 1269.5 | 759.5 | 958.5 | 11% |
| 250 | 2761.5 | 1817.7 | 3331.9 | 1949.6 | 2465 | 28.4% |
| 125 | 3665.6 | 3012.1 | 4430.2 | 2859.4 | 3491.8 | 40.3% |
| | YS inj. mouse | | | | mean | |
| pHA, m | 577.6 | 96.0 | 38.6 | | | |
| cells, m | 951.7 | 889.7 | 648.6 | | | |
| Cells, PHA | 5161.5 | 6951.7 | 4502.0 | | 5530.4 | |
| 500 | 1201.1 | 954.6 | 1201.0 | | 1118.9 | 20% |
| 250 | 2119.8 | 1164.1 | 2621.6 | | 1968.5 | 35.5% |
| 125 | 4277.5 | 1688.1 | 2488.1 | | 2817.9 | 50.9% |

We also observed that bone marrow cells from transgenic mice were able to resist G418, but we did not quantify the resistance.

EXAMPLE 8

Three weeks after injection of transformed YS cells, the bone marrow cells from the treated animal were lysed, and the lysate was analyzed by the method of Eglitis, et al., Science, 230: 1395, 1397 (Dec. 20, 1985) and Reiss, et al., Gene 30:211 (1984). Lysates were electrophoresed on a nondenaturing polyacrylamide gel. The gel was overlayed with agarose containing kanamycin at 25 ug/ml and 2 nM gamma-$^{32}$P-ATP (greater than 5000 Ci/mmol). The gel was blotted with Whatman P81 phosphocellulose paper. After washing to remove the ATP, autoradiography (FIG. 1) revealed the presence of the radiolabeled gamma phosphate group if the neomycin resistance enzyme (a phosphotransferase) transferred it to the kanamycin substrate.

Referring to FIG. 1, lanes 1 and 10 are psi-2. Lane 2 is cultured mouse yolk sac cells (untransfected); lane 3, bone marrow of transformed YS cell-injected animals; lane 5, the bone marrow control; lane 6, the spleen control; lane 7, brain cells transfected with psi-2 supernate; lane 8, brain cells pre-treated with polybrene and transfected with psi-2 supernate; and lane 9, transformed YS cells pre-treated with polybrene and transfected with psi-2 supernate. (Polybrene is used to enhance retroviral infection). It will be seen from FIG. 1 that lanes 1, 3, 9 and 10 are heavily marked. The light bands in other lanes are indicative of basal levels of phosphotransferase activity.

This evidences the transfer of a genetic trait to the bone marrow cell population by a cellular genetic delivery system.

EXAMPLE 9

Two days after injection, the YS cells were found in the bone marrow. On the third day they were found in the spleen. By one week after injection, the YS cells could no longer be distinguished morphologically from the surrounding tissue. However, as noted in Examples 6 and 7, bone marrow and spleen cells still exhibited neomycin resistance, even several weeks after injection. This suggests that the injected cells engaged in "catch-up" differentiation, rapidly differentiating into the target tissue.

EXAMPLE 10

The uterus of a pig was removed by hysterectomy at day 20, yielding 17 embryos. The yolk sacs revealed visible islets. Yolk sac cells were isolated and cultured by the previously described techniques, both with and without glycine treatments. The same five YS cell types were observable. These have been maintained in mixed cultures.

Pig forebrain and midbrain cells were also cultured.

It is believed that it may be preferable to use day 18 embryos, since the day 20 pig embryos appeared to be more advanced in development than the day 8 mouse embryos.

Considerable literature exists on comparative embryology which may be used to identify appropriate embryos to use in developing genetic delivery systems for other animals. Thus, for the yolk sac cell approach, one would look for an embryo with a fully developed yolk sac in which blood islets, though extant, are not visible at low magnification.

Thus, according to Tiedemann, Cell Tiss. Res., 173:109 (1976) the yolk sac of the cat is formed by the inner endodermal lining, by a vascular mesenchyme, and by a mesotheliuim on the outer face. In the cat, the mesenchyme is the site of blood islands or intravascular hematopoietic foci from the 14th until about the 38th day. Thus, one would try to culture yolk sac cells of 12-15 day cat embryos.

For the intracranial delivery approach, one would look for an embryo in which the neural fold is closed (or virtually so) and the fore-, mid, and hindbrains are evident. Thus day 8 in the mouse is comparable to about day 19 in man.

The term "animal", as used herein, includes humans. However, it is recognized that special legal and ethical considerations apply to human gene therapy. Human yolk sac cells may be obtained from a human abortus.

The term "transgenic animal" is used herein in its broad sense to include all animals in which at least some somatic cells contain heterologous DNA deliberately introduced into the cells. It is of course feasible to deliver new genetic material into germ cells as well as somatic cells. The term "chimeric animal" is used herein to refer to animals on which the new genetic material is found in some but not all cells. The term "tissue-specific chimeric animal" indicates that the new genetic material is found is some tissues and not in others.

There is no limitation on the gene which may be transferred by the method of this invention.

Growth hormone genes may be used to enhance growth rate, increase the efficiency of food utilization, increase lactation, or reduce fat on carcasses. The gonadotropin releasing hormone gene may be used for biosterilization. Synthetic genes encoding antigenic proteins may be used to assure heightened immune response. Lymphokine genes may have value in enhacing resistance to viruses, tumors and other challenges. Gonadotropin genes may be used to enhance ovulation and increase fertility. Genes regulating fatty acid synthetase or lipase production may be used to affect the lipid content of animal products. The genes transferred may be of genomic, cDNA, synthetic or mixed origin, and of natural or modified sequence.

Any embryonic tissue may be used to deliver genetic material to tissue of the same lineage in a target animal. It is recognized that the term "embryo", strictly speaking, does not include the yolk sac. However, for the purpose of these specifications and claims, the terms "embryo" or "embryonic tissue" are intended to include all prefetal cells derived from the ICM of the blastocyst, including the yolk sac.

It is not necessary to use cells of a single cell type as the genetic delivery system. Thus, one could use a mixed culture of all the yolk sac cells, pure cultures of any of the primary yolk sac cell types, or immortalized mixed or pure cell lines.

By selecting embryonic tissue of appropriate competency, it is possible to achieve any desired degree of specificity in targeting the tissues of the recipient animal. For example, one might target all ectodermal tissues, or merely the neural cells.

Reference to cells "derived" from embryonic cells is intended to encompass in vitro cell cultures of embryonic cells and the result of development after introduction of these cultured cells into a recipient animal, but not cells of a postnatal animal derived from embryonic cells by normal development in vivo.

While retroviral introduction of exogenous DNA into the embryonic carrier cells is preferred, the DNA may also be introduced by microinjection. It is also within the contemplation of this invention that the exogenous DNA be microinjected into the early embryonic cells (such as the one cell embryo) which will develop into the preferred yolk sac carrier cells of this invention. Also, it is possible to microinject an embryo with exogenous DNA, implant the embryo and permit it to develop into a transgenic mammal (all of whose cells are transformed with the exogenous DNA), breed the mammal to obtain already transformed embryonic cells, and isolate and culture the carrier (e.g., yolk sac, brain) cells of this daughter embryo.

The following cell lines were deposited under the Budapest Treaty with the American Type Culture Collection on Dec. 10, 1986:

| | |
|---|---|
| CRL 9289 | MBR CL1<br>A clonal line of mouse brain fibroblast cells. |
| CRL 9290 | MBRP -<br>A mixed cultre of mouse brain fibroblast cells. |
| CRL 9291 | MYS CL1<br>A clonal line of mouse yolk sac cells of type 3, subtyped "3a" because of its fibroblast character. |
| CRL 9292 | MYS CL2<br>A clonal line of mouse yolk sac cells of type 3, subtyped "3b" because of its epithelial character. |
| CRL 9293 | MYSP -<br>A mixed culture of yolk sac | cells.

The deposit of these lines should not be constructed as a license to make, use or sell the subject matter claimed herein.

The cell lines deposited hereunder, and cell lines derived therefrom by mutation or otherwise, are of value as carrier cells.

We claim:

1. A method of providing tissue-specific expression of exogenous genetic material is selected tissues of a recipient mammal which comprises:
   (a) providing carrier cells capable of selectively delivering said exogenous genetic material to said tissues, said cells selected from the group consisting of embryonic yolk sac cells, embryonic midbrain cells and embryonic forebrain cells, all of which are derived from a donor mammal of the same species, said cells also having been transformed in vitro with said exogenous genetic material and
   (b) introducing said cells into said recipient mammal in a manner permitting them to differentiate into said tissues.

2. The method of claim 1, where the carrier cells are mesodermal cells of the yolk sac which are competent to develop into hematopoietic stem cells, and the cells are introduced intravenously.

3. The method of claim 1, where the carrier cells are embryonic forebrain or midbrain cells.

4. The method of claim 1, where the cells are transformed with a retroviral vector carrying the genetic material.

5. The method of claim 4, where the retroviral vector is amphotrophic.

6. The method of claim 1 where the animal is immunocompetent and the introduction of the carrier cells does not result in an immune response.

7. The method of claim 1, said cells being essentially histocompatible with a host of the same species as the mammal from which the embryonic cells were derived.

8. The method of claim 1 in which the embryonic cells provided have been immortalized.

9. The method of claim 1, wherein the cells of the tissue are deficient in said genetic material.

10. The method of claim 1, where the cells are transformed by microinjecting them with the genetic material.

11. The method of claim 1 wherein the carrier cells are at a sufficiently early stage of development so that introduction of the carrier cells into an immunocompetent mammal does not result in an immune response to said carrier cells.

12. The method of claim 11 wherein the mammal is immunocompetent.

13. The method of claim 1 wherein the carrier cells are yolk sac cells derived from yolk sacs extracted from an embryonic donor mammal prior to the formation of blood islands visible at 12X magnification.

14. A process for producing a chimeric mammal characterized by the presence of heterologous genetic material in selected tissues of said mammal, which comprises introducing heterologous genetic material into said tissues by the method of claim 1.

15. The method of claim 1 wherein the carrier cells are provided in a non-enzymatically disaggregated form.

* * * * *